United States Patent
Donegan

(10) Patent No.: US 10,543,007 B2
(45) Date of Patent: Jan. 28, 2020

(54) CAVITATION CATHETER

(71) Applicant: Medtronic Vascular, Inc., Santa Rosa, CA (US)

(72) Inventor: Michael Donegan, Galway (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 88 days.

(21) Appl. No.: 15/475,203

(22) Filed: Mar. 31, 2017

(65) Prior Publication Data
US 2018/0280043 A1 Oct. 4, 2018

(51) Int. Cl.
*A61B 17/22* (2006.01)
*A61M 25/00* (2006.01)

(52) U.S. Cl.
CPC .. *A61B 17/22004* (2013.01); *A61B 17/22012* (2013.01); *A61M 25/0045* (2013.01); *A61M 25/0052* (2013.01); *A61B 2017/22007* (2013.01); *A61B 2017/22025* (2013.01); *A61B 2017/22064* (2013.01); *A61B 2017/22065* (2013.01)

(58) Field of Classification Search
CPC ...... A61B 17/2204; A61B 2017/22005; A61B 2017/22007; A61B 2017/22008; A61B 2017/22009; A61B 2017/22011; A61B 2017/22025; A61M 25/0032; A61M 25/0023; A61M 25/0045; A61M 25/005; A61M 25/0052; A61M 2025/1047
See application file for complete search history.

(56) References Cited

U.S. PATENT DOCUMENTS

| 2001/0044591 A1* | 11/2001 | Stevens | A61F 2/2427 604/6.11 |
| 2005/0038406 A1* | 2/2005 | Epstein | A61M 25/00 604/500 |
| 2006/0020256 A1* | 1/2006 | Bell | A61M 25/0045 604/523 |

(Continued)

FOREIGN PATENT DOCUMENTS

WO 9713543 A1 4/1997
WO 2009042621 A2 4/2009

OTHER PUBLICATIONS

International Search Report and Written Opinion of International Application No. PCT/US2018/024780, dated Jul. 10, 2018, 14 pp.

(Continued)

*Primary Examiner* — Wade Miles
(74) *Attorney, Agent, or Firm* — Shumaker & Sieffert, P.A.

(57) ABSTRACT

In some examples, a catheter includes an elongated body configured for navigation through vasculature of a patient, the elongated body having an inner wall that defines a lumen extending from a proximal portion to a distal portion. The elongated body is configured to pass a fluid through the lumen and out a distal end of the elongated body. At the distal portion, the inner wall defines a convergent-divergent region such that a diameter of the lumen while moving distally within the elongated body converges from a first lumen diameter to a second lumen diameter and then diverges from the second lumen diameter to a third lumen diameter. The convergent-divergent region is configured to cause a fluid flowing through the lumen to cavitate as the fluid flows through the convergent-divergent region.

33 Claims, 3 Drawing Sheets

(56) References Cited

U.S. PATENT DOCUMENTS

2011/0276024 A1 11/2011 Randolph et al.
2012/0095371 A1* 4/2012 Sverdlik ............ A61B 17/2202
601/2

OTHER PUBLICATIONS

Brujan, Emil Alexandru, "Cardiovascular Cavitation" Medical Engineering & Physics 31, May 2009, pp. 742-751.

* cited by examiner

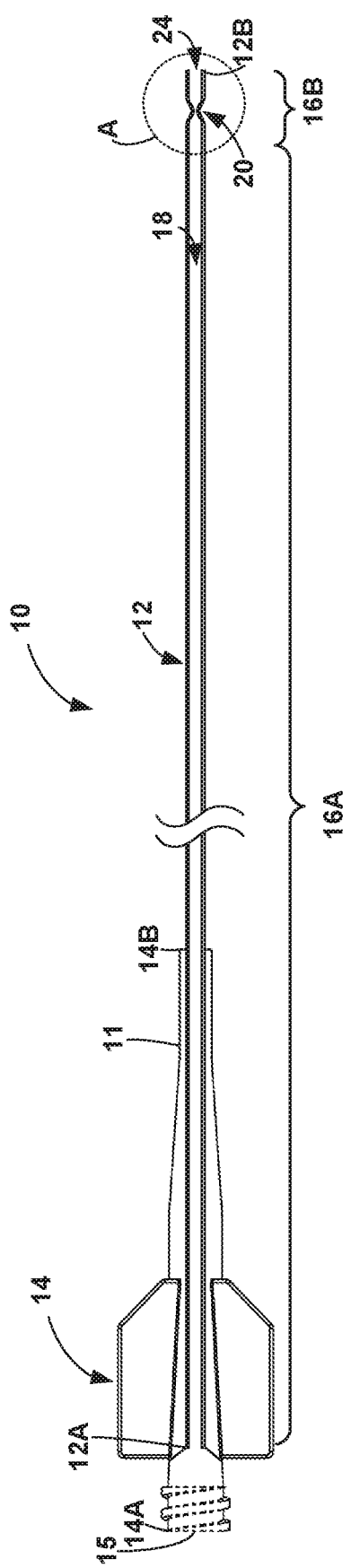
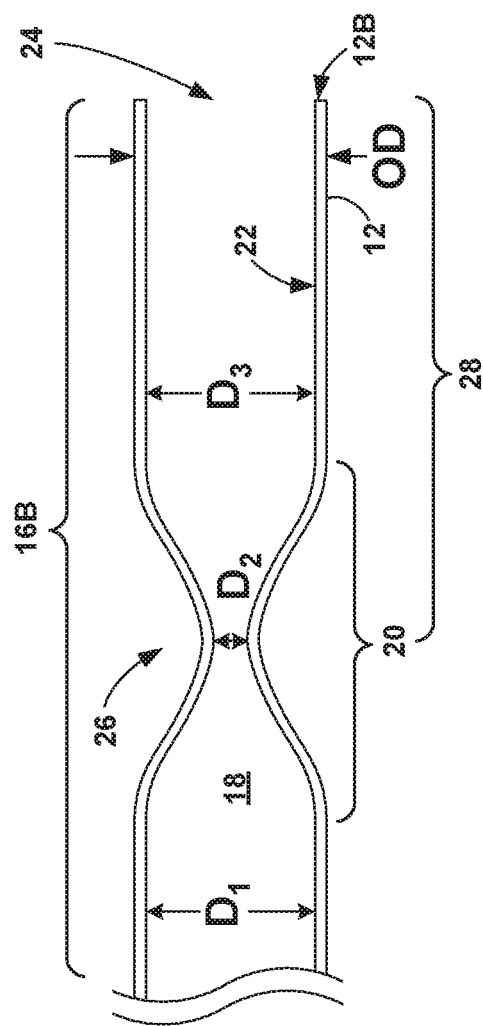
FIG. 1
FIG. 2

CAVITATION CATHETER

TECHNICAL FIELD

This disclosure relates to a medical catheter.

BACKGROUND

A medical catheter defining at least one lumen has been proposed for use with various medical procedures. For example, in some cases, a medical catheter may be used to access and treat defects in blood vessels, such as, but not limited to, lesions or occlusions in blood vessels.

SUMMARY

In some aspects, this disclosure describes example medical devices, such as catheters, that define a convergent-divergent region configured to cause fluid flowing through a lumen of the medical device to cavitate as the fluid flows through the convergent-divergent region. The medical device may be used to treat a lesion within a vasculature of a patient by, for example, passing a fluid through the convergent-divergent region of the device to cause the fluid to cavitate and implode, thereby creating a shockwave. The shockwave may impact the lesion, which may dislodge a portion of the lesion. This disclosure also describes example methods of forming such medical devices and methods of using the devices.

Clause 1: In one example, a catheter includes an elongated body configured for navigation through vasculature of a patient, the elongated body including an inner wall that defines a lumen extending from a proximal portion to a distal portion, the elongated body configured to pass a fluid through the lumen and out a distal end of the elongated body where at the distal portion of the elongated body, the inner wall defines a convergent-divergent region such that a diameter of the lumen while moving distally within the elongated body converges from a first lumen diameter to a second lumen diameter and then diverges from the second lumen diameter to a third lumen diameter with the convergent-divergent region is configured to cause the fluid flowing through the lumen to cavitate as the fluid flows through the convergent-divergent region.

Clause 2: In some examples of the catheter of clause 1, the convergent-divergent region includes a cavitation region defined by the inner wall, the cavitation region having a length of at least about 0.5 millimeters (mm) with the length of cavitation region being an axial distance from a point where the second lumen diameter begins to diverge to the third lumen diameter to the distal end of the elongated body.

Clause 3: In some examples of the catheter of clause 2, the cavitation region includes at least one radiopaque marker.

Clause 4: In some examples of the catheter of clause 1, a ratio of the third lumen diameter to the second lumen diameter is at least about 2.5:1.

Clause 5: In some examples of the catheter of clause 1, the elongated body defines a substantially continuous outer diameter along the convergent-divergent region.

Clause 6: In some examples of the catheter of clause 1, the elongated body defines an outer diameter along the convergent-divergent region having an hour-glass shape.

Clause 7: In some examples of the catheter of clause 1, further including a balloon connected to the elongated body proximal to the convergent-divergent region.

Clause 8: In some examples of the catheter of clause 1, the elongated body further includes a structural support element at the convergent-divergent region, the structural support element includes at least one of a wire braid or a coil.

Clause 9: In some examples of the catheter of clause 8, the convergent-divergent region includes a neck section defined by the second lumen diameter, the structural support element surrounds the inner wall of the convergent-divergent region at the neck section.

Clause 10: In some examples of the catheter of clause 1, further including an outer casing positioned over the inner wall, the outer casing defines a substantially continuous outer diameter of the catheter along the convergent-divergent region.

Clause 11: In some examples of the catheter of clause 10, the convergent-divergent region includes a neck section defined by the second lumen diameter, a region between the inner wall at the neck section and the outer casing includes an elastic or inelastic fill material.

Clause 12: In some examples of the catheter of clause 1, the elongated body includes at least one protuberance extending into the lumen within the convergent-divergent region, the at least one protuberance is configured to agitate the flow of the fluid that passes through the lumen.

Clause 13: In some examples of the catheter of clause 12, the at least one protuberance includes a ridge, a fin, a divot, a bump, or a ripple in the inner wall.

Clause 14: In one example, an assembly includes a catheter including an elongated body configured for navigation through vasculature of a patient, the elongated body including an inner wall that defines a lumen extending from a proximal portion to a distal portion, the elongated body configured to pass a fluid through the lumen and out a distal end of the elongated body, at the distal portion of the elongated body the inner wall defines a convergent-divergent region such that a diameter of the lumen while moving distally within the elongated body converges from a first lumen diameter to a second lumen diameter and then diverges from the second lumen diameter to a third lumen diameter; and a pump assembly connected to the proximal portion of the elongated body of the catheter and configured to pump a fluid through the lumen of the elongated body and out an opening at the distal end of the elongated body, the convergent-divergent region of the elongated body is configured to cause the fluid flowing through the lumen to cavitate as the fluid flows through the convergent-divergent region.

Clause 15: In some examples of the assembly of clause 14, the convergent-divergent region of the elongated body is configured to cause the fluid flowing at a flow rate of at least 1 cubic centimeters per second (cc/s) to about 20 cc/s to cavitate as the fluid flows through the convergent-divergent region.

Clause 16: In some examples of the assembly of clause 14, a ratio of the third lumen diameter to the second lumen diameter is at least about 2.5:1.

Clause 17: In some examples of the assembly of clause 14, the convergent-divergent region includes a cavitation region defined by the inner wall having a length of at least about 0.5 mm, the length of cavitation region is an axial distance from a point where the second lumen diameter begins to diverge to the third lumen diameter to the distal end of the elongated body.

Clause 18: In some examples of the assembly of clause 14, the elongated body defines a substantially continuous outer diameter over the convergent-divergent region.

Clause 19: In some examples of the assembly of clause 14, the elongated body further includes a structural support element at the convergent-divergent region, the structural support element including at least one of a wire braid or a coil.

Clause 20: In some examples of the assembly of clause 19, the elongated body further including an outer casing positioned over the inner wall and the structural support element, the outer casing defines a substantially continuous outer diameter over the convergent-divergent region.

Clause 21: In some examples of the assembly of clause 14, the elongated body includes at least one protuberance extending into the lumen within the convergent-divergent region, the at least one protuberance is configured to agitate the flow of the fluid that passes through the lumen.

Clause 22: In one example, a method that includes positioning a distal end of a catheter adjacent to a lesion within a vasculature of a patient, the catheter includes an the elongated body including an inner wall that defines a lumen extending from a proximal portion to a distal portion, the elongated body configured to pass a fluid through the lumen and out a distal end of the elongated body, at the distal portion of the elongated body, the inner wall defines a convergent-divergent region such that a diameter of the lumen while moving distally within the elongated body converges from a first lumen diameter to a second lumen diameter and then diverges from the second lumen diameter to a third lumen diameter; and injecting a fluid into the lumen of the elongated body, injecting the fluid into the lumen causes the fluid to cavitate as the fluid flows through the convergent-divergent region of the elongated body to form bubbles, the bubbles implode prior to the bubbles exiting out the distal end of the elongated body.

Clause 23: In some examples of the method of clause 22, injecting the fluid into the lumen of the elongated body includes injecting the fluid at a flow rate of about 1 cubic centimeters per second (cc/s) to about 20 cc/s.

Clause 24: In some examples of the method of clause 22, injecting the fluid into the lumen of the elongated body includes injecting saline.

BRIEF DESCRIPTION OF THE DRAWINGS

FIG. 1 is a schematic cross-sectional view of an example catheter that includes a convergent-divergent region in a distal portion of an elongated body, where the cross-section is taken along a longitudinal axis of the elongated body.

FIG. 2 is an enlargement of segment-A of FIG. 1, showing a schematic cross-sectional view of the convergent-divergent region at distal portion of the elongated body, where the cross-section is taken along a longitudinal axis of the elongated body.

Figure 3:
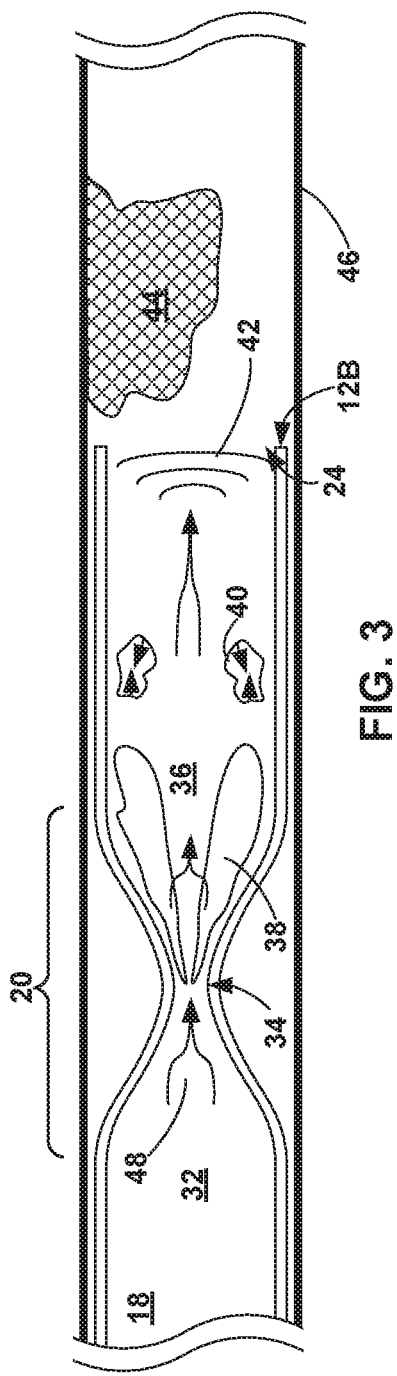
FIG. 3 is a schematic illustration of the described cavitation process.

The details of one or more aspects of the disclosure are set forth in the accompanying drawings and the description below. Other features, objects, and advantages of the techniques described in this disclosure will be apparent from the description and drawings, and from the claims.

DETAILED DESCRIPTION

The disclosure describes medical devices (e.g., catheters) that include a relatively flexible elongated body (e.g., the body of the catheter) that is configured to be navigated through vasculature of a patient to a treatment site that contains a lesion within the vasculature. The lesion can be calcified in some cases. Calcified lesions can cause partial or full blockages of blood bearing vessels, which can result in adverse physiological effects to the patient. Such lesions may be very hard and difficult to treat using traditional methods, such as balloon angioplasty, stenting, thrombectomy, atherectomy, or other interventional procedures. The medical devices described herein are primarily referred to as catheters, but can include other medical devices.

The catheters described herein may include an elongated body that defines a lumen extending from a proximal portion to a distal portion, the lumen having a convergent-divergent region. In the convergent-divergent region of the catheter, a diameter of the lumen while moving distally within the elongated body may converge from a first lumen diameter to a second lumen diameter and then diverge from the second lumen diameter to a third lumen diameter. The convergent-divergent region is configured to cause the fluid flowing through the lumen to cavitate as the fluid flows (in a distal direction) through the convergent-divergent region.

Using the medical devices and techniques described herein, a fluid (e.g., saline) can be passed under pressure through the converging-diverging region within the elongated body to cavitate the fluid to form cavitation bubbles due to the sudden drop in pressure of the liquid flowing through the convergent-divergent region. As the pressure normalizes, the bubbles implode, releasing energy in the form of heat and a pressure shockwave. The pressure shockwave may progress through the lumen of the elongated body and out an ejection port at a distal end of the elongated body. When the distal end of the elongated body is positioned proximate to a calcified lesion, the pressure shockwave, upon exiting the distal end of the elongated body, may impact the calcified lesion to dislodge and break-up at least part of the lesion. This treatment of the calcified lesion may help open up the blood vessel of the patient.

FIG. 1 is a schematic cross-sectional view of an example catheter 10, which includes an elongated body 12, a hub 14 positioned at a proximal end 12A of elongated body 12, and a convergent-divergent region 20 in a distal portion 16B of elongated body 12. The cross-sectional view of FIG. 1 is taken along a longitudinal axis of elongated body 12. Elongated body 12 may extend from proximal end 12A to distal end 12B, and define a proximal portion 16A and distal portion 16B with an inner lumen 18 that extends the length of elongated body 12 from proximal end 12A to distal end 12B having an ejection port 24. Ejection portion 24 may be, for example, an opening defined by elongated body 12 at distal end 12B.

FIG. 2 is an enlargement of segment-A of FIG. 1 showing a cross-sectional view of convergent-divergent region 20 at distal portion 16B of elongated body 12, where the cross-section is taken along the longitudinal axis of elongated body 12. At distal portion 16B, an inner wall 22 of elongated body that defines inner lumen 18 defines convergent-divergent region 20, which is configured such that while moving distally within elongated body 12, the diameter of inner lumen 18 converges and diverges at different diameters. As described further below, convergent-divergent region 20 may be configured to allow a fluid to pass through inner lumen 18 and convergent-divergent region 20 to exit through ejection port 24 at distal end 12B. As the fluid passes through convergent-divergent region 20, the fluid may undergo cavitation (e.g., formation of bubbles) followed by the implosion of the cavitation bubbles, which creates a pressure shockwave that progresses through lumen 18 and out ejection port 24 at distal end 12B.

In the example shown in FIG. 1, proximal end 12A of catheter 12 is received within hub 14 and can be mechanically connected to hub 14 via an adhesive, welding, or another suitable technique or combination of techniques. Opening 15 defined by hub 14 and located at proximal end 14A of hub 14 is aligned with the inner lumen 18 of elongated body 12, such that the inner lumen 18 of elongated body 12 may be accessed via opening 15. In some examples, catheter 10 may include a strain relief body 11, which may be a part of hub 14 or may be separate from hub 14. Additionally or alternatively, proximal portion 16A of catheter 10 can include another structure in addition or instead of hub 14. For example, catheter hub 14 may include one or more luers or other mechanisms for establishing connections between catheter 10 and other devices.

Hub 14 may define an opening through which an inner lumen 18 of elongated body 12 may be accessed for passing a cavitation fluid, another fluid, or a device (e.g., another catheter, stent, or the like) through lumen 18. In some examples, hub 14 may be configured to receive a fluid delivery mechanism for delivering a cavitation fluid through lumen 18 including convergent-divergent region 20. Any suitable delivery mechanism may be used including, for example, an injection syringe; an infusion pump such as a mechanical or electrical pump, peristaltic pump, or the like; a digital subtraction angiography (DSA) high pressure injection device; or the like.

In some examples elongated body 12 of catheter 10 may be used to access relatively distal vasculature locations in a patient or other relatively distal tissue sites (e.g., relative to the vasculature access point). Example vasculature locations may include, for example, locations in the cerebral vasculature or a coronary artery. In some examples, elongated body 12 is structurally configured to be relatively flexible, pushable, and relatively kink- and buckle-resistant, so that it may resist buckling when a pushing force is applied to a relatively proximal portion of catheter 10 to advance elongated body 12 distally through vasculature, and so that it may resist kinking when traversing around a tight turn in the vasculature. Unwanted kinking and/or buckling of elongated body 12 may hinder a clinician's efforts to push the catheter body distally, e.g., past a turn in the vasculature.

Elongated body 12 has a suitable length for accessing a target tissue site within the patient from a vasculature access point. The length may be measured along the longitudinal axis of elongated body 12. In some examples the working length of elongated body 12 may be measured from hub distal end 14B of hub 14 (marked by the distal end of optional strain relief body 11) to distal end 12B of distal portion 16B. The working length of elongated body 12 may depend on the location of lesion 44 (FIG. 3) within vasculature 46. For example, if catheter 10 is a distal access catheter used to access vasculature in a brain of a patient from a femoral artery access point at the groin of the patient, catheter 10 may have a working length of about 129 centimeters (cm) to about 135 cm, such as about 132 cm, although other lengths may be used. In other examples, or for other applications, the working length of elongated body 12 may have different lengths.

In some examples, one or more portions of elongated body 12 may be include a structural support member, e.g., a wire braid, coil, or both a braid and coil (not shown), configured to increase the structural integrity of elongated body 12 while allowing elongated body 12 to remain relatively flexible. For example, the structural support member may be configured to help elongated body 12 substantially maintain its cross-sectional shape substantially throughout proximal and distal portions 16A and 16B or at least help prevent elongated body 12 from buckling or kinking as it is navigated through tortuous anatomy. As a result, a clinician may apply pushing forces, rotational forces, or both, to proximal portion 16A of elongated body 12, and such forces may cause distal portion 16B of elongated body 12 to advance distally, rotate, or both, respectively. Materials that may be used to for the support member include, for example, metals, such as stainless steel or a nickel-titanium alloy (e.g., Nitinol). Example structural support members are described in U.S. patent application Ser. No. 13/878,890 entitled Distal Access Aspiration Guide Catheter, which is hereby incorporated by reference in its entirety.

As shown in FIG. 2, inner wall 22 of elongated body 12 defines convergent-divergent region 20 such that while moving distally within elongated body 12 (e.g., towards distal end 12B), the diameter of inner lumen 18 converges from a first lumen diameter ($D_1$) to a narrower second lumen diameter ($D_2$) and then diverges from the second lumen diameter ($D_2$) to a third lumen diameter ($D_3$). In some examples, the portion of inner lumen 18 defining second diameter ($D_2$) may be referred to as the "neck" section of convergent-divergent region 20, the neck section representing the narrowest portion (e.g., smallest diameter) of convergent-divergent region 20.

The first, second, and third lumen diameters ($D_1$, $D_2$, $D_3$) of inner lumen 18 may be sized such that fluid (e.g., saline) flowing through convergent-divergent region 20 causes the fluid to cavitate (e.g., form bubbles). FIG. 3 shows an example schematic illustration of the described cavitation process. As fluid 48 flows in a distal direction through convergent-divergent region 20 at a selected volumetric flow rate, the velocity of fluid 48 will increase as the fluid moves from convergent section 32 defined by the first lumen diameter ($D_1$) into the neck section 34 defined by the second lumen diameter ($D_2$) due to the reduction in the cross-sectional area between convergent section 32 to the neck section 34. This increase in fluid velocity results in a decrease in the hydrostatic pressure of fluid 48 as the fluid enters neck section 34 in accordance with Bernoulli's Equation:

$$P_1 + \tfrac{1}{2}\rho v_1^2 + \mu g h_1 = P_2 + \tfrac{1}{2}\rho v_2^2 + \mu g h_2 \quad [1]$$

where P represents hydrostatic pressure of the fluid for a given point, v represents the velocity of the fluid for a given point, h represents the height of the fluid for a given point, $\rho$ is the density of the fluid, and g is the gravitational constant, assuming laminar flow for the system. For practical applications of catheter 10, the potential energy component (of Equation 1) may be assumed as constant, or having negligible effect on the cavitation process across convergent-divergent region 20, thereby reducing Equation 1 as follows.

$$P_1 + \tfrac{1}{2}\rho v_1^2 = P_2 + \tfrac{1}{2}\rho v_2^2 \quad [2]$$

In accordance with Equation 2, as fluid 48 flows from convergent section 32 into the neck section 34, the velocity of fluid 48 will increase, thereby reducing the hydrostatic pressure of fluid 48 within neck section 34. Convergent-divergent region 20 may be sized such that for a target flow rate and fluid 48 (e.g., about 1 cc/sec to about 20 cc/sec), the velocity increase of fluid 48 through neck section 34 causes the hydrostatic pressure of fluid 48 within neck section 34 to drop below the vapor pressure of fluid 48, thereby causing the fluid to undergo cavitation (e.g., form gaseous bubbles 38 of reduced pressure). The pressure drop can be generally increased by increasing the differences in velocity between convergent section 32 and neck section 34, thereby increasing the amount of cavitation. In some examples, this can be accomplished by increasing the volumetric flow rate of fluid 48 through convergent-divergent region 20 or by increasing the difference between first and second lumen diameters ($D_1$, $D_2$). If the difference between first and second lumen diameters ($D_1$, $D_2$) is increased then the change in fluid velocity also increases between first and second lumen diameters ($D_1$, $D_2$) thereby increasing the amount of cavitation.

As fluid 48 progresses distally within inner lumen 18 towards distal end 12B, gaseous bubbles 38 and fluid 48 will transition from neck section 34 into divergent section 36 defined by the part of lumen 18 having third lumen diameter ($D_3$). For a given flow rate, the change in cross-sectional area between neck section 34 and divergent section 36 will cause the velocity of fluid 48 within the transition from neck section 34 into divergent section 36 to decrease and hydrostatic pressure of fluid 48 to increase as the fluid enters divergent section 36. The increase in hydrostatic pressure within divergent section 36 causes gaseous bubbles 38 to implode 40, releasing energy in the form of heat and a pressure shockwave 42. In some examples, pressure shockwave 42 may be omni-directional, however, as a result of the flow direction of fluid 48, shockwave 42 will progress distally to emerge from ejection port 24 at distal end 12B. As shown in FIG. 3, when distal end 12B is positioned proximate to calcified lesion 44, shockwave 42 may impact calcified lesion 44 within vasculature 46. In some examples, the energy associated with shockwave 42 impacting calcified lesion 44 may cause at least a portion of lesion 44 to be dislodged from vasculature 46. In some examples, divergent section 36 may include one or more optional side ports (not shown) in the body of the catheter 10 to allow some of pressure shockwave 42 to pass through the side port for treating other areas along the vasculature surface.

As shown in FIG. 3, distal end 12B of elongated body 12 may be positioned near lesion 44 to ensure shockwave 42 is incident on lesion 44 as opposed to other portions of vasculature 46. In some examples, the relative length of elongated body 12 distal to convergent-divergent region 20 (e.g., divergent section 36) may assist in delivering the energy of shockwave 42 towards lesion 44. For example, the relative length of elongated body 12 distal to convergent-divergent region 20 may be sized such that gaseous bubbles 38 are allowed to completely implode 40 within lumen 18 before fluid 48 exits distal end 12B, thereby preventing the generation of shockwave 42 along regions of vasculature 46 distal to calcified lesion 44.

In other examples, the relative length, construction, or material selection of elongated body 12 distal to convergent-divergent region 20 may be configured to reduce or even prevent shockwave 42 from impacting portions of vasculature 46 that are not intended to receive treatment. For example, divergent section 36 of elongated body 12 distal to convergent-divergent region 20 may be configured to absorb at least a portion of the radial disbursements of shockwave 42 (e.g., portions of shockwave 42 directed radially outward from the central axis of elongated body 12) as gaseous bubbles 38 undergo implosion 40. The absorption of at least a portion of the radial disbursements of shockwave 42 may occur because as shockwave 42 contacts the inner wall of elongated body 12, the energy of shockwave 42 may be reduced. Additionally or alternatively, divergent section 36 of elongated body 12 distal to convergent-divergent region 20 may be configured to reflect such radial disbursements of shockwave 42, allowing the shockwaves to propagate within divergent section 36 towards distal end 12B. Reducing the impact that shockwave 42 may have on portions of vasculature 46 that are not intended to receive treatment may help prevent shockwave 42 from inadvertently affecting these portions of vasculature 46. Suitable materials for divergent section 36 may include polymeric materials such as robust thermoplastics, polyether block amides, polyamides, combinations thereof or the like. In some examples, divergent section 36 may include a support member (e.g., wire braid) to increase the robustness of divergent section 36 towards radial pressure distributions attributed to shockwave 42. Additionally or alternatively, the thickness of the catheter wall in divergent section 36 may be increased to absorb or reflect radial distributions of shockwave 42.

In some examples, the region of elongated body 12 distal to neck section 34 may be characterized as the cavitation region 28 of catheter 10. Cavitation region 28 may have an axial length that measures the distance between distal end 68 and the point where the second lumen diameter ($D_2$) begins to diverge to the third lumen diameter ($D_3$). The axial length may be measured along a longitudinal axis of elongated body 12. In some examples, cavitation region 28 may have an axial length (length extending along the central axis of elongated body 12) of about 0.5 mm to about 3 mm. A shorter axial length may permit more of pressure shockwave 42 to be delivered into vasculature 46. In some examples, cavitation region 28 may have an axial length of about 1 mm to about 3 mm.

In some examples, divergent section 36 may include one or more side ports (not shown) for receiving, for example, a guide member (e.g. guidewire) or a filtration device. The guide member may be used to guide elongated body 12 to a treatment site within the vasculature of a patient. For example, the guide member may first be positioned within the vasculature, and elongated body 12 may be guided to the treatment site over the guide member.

A filtration device may include a filter element that is repositionable between a collapsed configuration and an expanded configuration configured for filtering pieces of the calcified lesion from the patient's vasculature. In some examples the filter element may include a plurality of filaments woven together such that the filtering device provides the desired characteristics of controlled pore size, high percentage of pore area, high collection capacity, patency, mechanical strength, low collapsed or retracted profile, and strength during recovery. In general, the filter device may have a conical or cup-shape that is open on a proximal end and closed at a distal end. The filter device may be connected to a guidewire configured to assist with one or more of the deployment or recapture of the filter device from the patient's vasculature.

In some examples in which a filtration device may be used with catheter 10, the filtration device can be housed within lumen 18 (e.g., within divergent section 36) during advancement of catheter 10 to a treatment site. In some examples, the filtration device may include a guidewire that extends substantially parallel to elongated body 12 and through the side port within the tubular wall of divergent section 36. Once catheter 10 is in position adjacent to a treatment site, the filtration device may be deployed distal to lesion 44 by advancing the associated guidewire relative to elongated body 12. The filtration device may then be used to collect portions of lesion 44 that dislodge during the cavitation procedure. Including the side port within a sidewall of divergent section 36 may allow the guidewire connected to the filtration device to exit lumen 18 distal of neck section 34, thereby preventing the guidewire from interfering with the cavitation process. In some examples, upon completion of the treatment procedure, the filtration device may be withdrawn into lumen 18 (e.g., within divergent section 36) and subsequently withdrawn from the patient. In other examples, another device (e.g., a retrieval catheter) may be used to withdraw the filtration device from the patient.

In some examples, at least one of the convergent section 32, neck section 34, or divergent section 36 of catheter 10 may include a radiopaque marker to help a clinician position convergent-divergent region 20 relative to lesion 44. For example, a radiopaque marker in the form of a full or partial ring of material more radiopaque than the material forming elongated body 12 may be positioned around or embedded in neck section 34, immediately proximal to distal end 12B, anywhere between neck section 34 and distal end 12B, or any combination thereof.

In some examples, the relative sizes of first, second, and third lumen diameters ($D_1$, $D_2$, $D_3$) may be dependent on the type of catheter 10 and size of vasculature 46 in which catheter 10 is introduced. In some examples, the relative change between first and second lumen diameters ($D_1$, $D_2$), and between second and third lumen diameters ($D_2$, $D_3$) should be as large as possible to establish cavitation using relatively low volumetric flow rates of fluid 48. In some examples, second lumen diameter ($D_2$) may be less than about 1 mm. Additionally or alternatively, second lumen diameter ($D_2$) may be sufficiently sized to receive a guidewire (e.g., a guidewire having a diameter of about 0.2 mm to about 0.8 mm (about 0.008 inches to about 0.030 inches)) to assist with the navigation of catheter 10 to a distal treatment site. In some examples, convergent section 32 defined by first lumen diameter ($D_1$) may define a diameter of about 1.5 mm, while neck section 34 defined by second lumen diameter ($D_2$) defines a diameter of about 0.57 mm.

In some examples, first and third lumen diameters ($D_1$, $D_3$) may be about 1.5 mm to about 3 mm. In some examples, first and third ($D_1$, $D_3$) lumen diameters may be substantially the same (e.g., the same or nearly the same). In other examples, first lumen diameter ($D_1$) may be less than third lumen diameter ($D_3$), or first lumen diameter ($D_1$) may be greater than third lumen diameter ($D_3$).

The transition between first, second, and third lumen diameters ($D_1$, $D_2$, $D_3$) may be of any suitable configuration. For example, as shown in FIG. 2, the transition may be relatively smooth resulting in a gradient change from the first lumen diameter to the second lumen diameter ($D_1$, $D_2$) and from the second lumen diameter to the third lumen diameter ($D_2$, $D_3$). In other examples, the transition from one or more of first, second, and third lumen diameters ($D_1$, $D_2$, $D_3$) may be relatively abrupt (e.g., a step change). Such abrupt changes may agitate the flow of the fluid through convergent-divergent region 20.

In some examples, the dimensions of convergent-divergent region 20 may be as described in terms of the ratio between the third and second lumen diameters ($D_3:D_2$). In some examples, the ratio between second and third lumen diameters ($D_3:D_2$) may be about 2.5:1. However, other ratios may also be used in other examples.

In some examples, first, second, and third lumen diameters ($D_1$, $D_2$, $D_3$) of convergent-divergent region 20 may be sized to cavitate fluid 48 at a relatively low flow rates. For example, cavitation of fluid 48 may be obtained at flow rates as low as about 1 cc/sec. Higher flow rates (e.g., about 20 cc/sec) may be used to establish a high degree of cavitation, however the flow rate of fluid 48 should remain below an amount that may inadvertently adversely affect portions of vasculature 46 that are not targeted for treatment. In some examples, fluid 48 may be delivered into lumen 18 as a continuous flowing stream or in bursts to dislodge lesion 44.

Fluid 48 may include any suitable fluid that is biocompatible and suitable for injecting into vasculature 46 of a patient and can be used to form cavitation bubbles 38. In some examples, using fluid 48 with a lower boiling point will result in a higher vapor pressure of fluid 48, thereby requiring less of a pressure drop to induce cavitation. In some examples, fluid 48 may include saline or similar solution with a salt content between about 0.9 weight percent (wt. %) and about 5 wt. %. In some examples, the lower the salt content of the saline fluid, the higher the vapor pressure will be for the fluid, thereby requiring less of a pressure drop to induce cavitation.

Additionally or alternatively, fluid 48 may be heated (e.g., body temperature or about 37° C.) prior to injection into lumen 18 and through convergent-divergent region 20. Heating a fluid increases the relative vapor pressure of the fluid. By increasing the temperature and vapor pressure of the fluid 48, the pressure difference observed between the vapor pressure of fluid 48 and the hydrostatic pressure of fluid 48 within neck section 34 may be increased, resulting in a greater degree of cavitation.

Convergent-divergent region 20 and other portions of elongated body 12 may be formed using any suitable materials. In some examples, convergent-divergent region 20 may be composed of relatively stiff materials compared to other portions of elongated body 12, where the material for convergent-divergent region 20 may be configured to withstand the pressure changes associated with fluid 48 flowing through neck section 34 without undergoing significant deformation. Such suitable materials may include, but are not limited to, polyether block amides, biocompatible metals (e.g. stainless steel), or the like.

In some examples, portions of elongated body 12, may include an inner liner forming the interior wall 22 of catheter 10. The inner liner may be lubricious in some examples in order to facilitate the introduction and passage of a device, e.g., a guidewire, an inner catheter, or another medical device, through inner lumen 18. Example materials for the inner liner may include, but are not limited to, polytetrafluoroethylene (PTFE), fluoropolymer, perfluoroalkyoxy alkane (PFA), fluorinated ethylene propylene (FEP), or any combination thereof.

In some examples, elongated body 12 may be formed from two or more discrete and separate longitudinally extending segments that are mechanically connected to each other, e.g., at axial butt joints. In some such examples, convergent-divergent region 20 may be formed independent of other portions of elongated body 12 through, for example, injection molding, and then welded or otherwise bonded to the other portions of elongated body 12.

The outer diameter (OD) of elongated body 12 may be of any suitable size or dimension. In some examples, the outer diameter may be substantially constant (e.g., uniform outer diameter), tapered (e.g. tapered or step change to define a narrower distal portion), or combinations thereof. In some examples, elongated body 12 of catheter 10 may have a relatively smaller outer diameter which may make it easier to navigate through a tortuous vasculature. In some examples, the outer diameter of elongated body 12 may taper from about 6 French (e.g., 6 French or nearly 6 French) at proximal end 12A to about 5 French (e.g., 5 French or nearly 5 French) at the distal end 12B (e.g., proximal to taper section 20). In other examples, the outer diameter of elongated body 12 may taper from about 4 French (e.g., 4 French or nearly 4 French) at proximal end 12A to about 5 French (e.g., 3 French or nearly 3 French) at the distal end 12B. In other examples, the outer diameter of elongated body 12 may remain substantially constant (e.g., constant or nearly constant) in the range of about 3 French and about 6 French. In some examples, the outer diameter of elongated body 12 may be larger than 6 French, for example 8 French. The measurement term French, abbreviated Fr or F, is three times the diameter of a device as measured in millimeters (mm). Thus, a 8 French diameter is about 2.67 mm, a 6 French diameter is about 2 mm, a 5 French diameter is about 1.67 mm, a 4 French diameter is about 1.33 mm, and a 3 French diameter is about 1 mm. In some examples, the outer diameter of elongated body 12 may be between about 1 mm to about 2.67 mm.

In some examples, the outer diameter (OD) of elongated body 12 may define an hour-glass shape 26 over convergent-divergent region 20. In other examples, as described further below, the outer diameter (OD) of elongated body 12 over convergent-divergent region 20 may be substantially continuous such that elongated body 12 exhibits a smooth or nearly smooth transition in the outer diameter (OD) from the proximal to distal sides of convergent-divergent region 20 absent of any curvature that may otherwise be formed by hour-glass shape 26.

In some examples, at least a portion of an outer surface of elongated body 12 includes one or more coatings, such as, but not limited to, an anti-thrombogenic coating, which may help reduce the formation of thrombi in vitro, an anti-microbial coating, and/or a lubricating coating. In some examples, the entire working length of elongated body 12 (from distal portion 14B of hub 14 to distal end 12B) is coated with the hydrophilic coating. In other examples, only a portion of the working length of elongated body 12 coated with the hydrophilic coating. This may provide a length of elongated body 12 distal to distal end 14B of hub 14 with which the clinician may grip elongated body 12, e.g., to rotate elongated body 12 or push elongated body 12 through vasculature. In some examples, the entire working length of elongated body 12 or portions thereof may include a lubricious outer surface, e.g., a lubricious coating. The lubricating coating may be configured to reduce static friction and/or kinetic friction between elongated body 12 and tissue of the patient as elongated body 12 is advanced through the vasculature.

Figure 4:
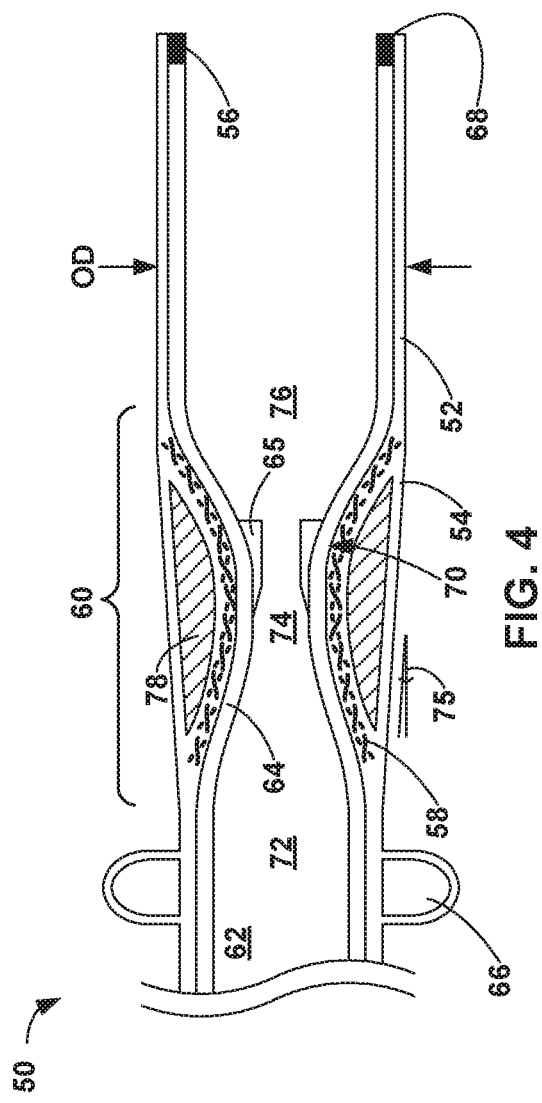
FIG. 4 is a cross-sectional view of a distal portion of another example of catheter that includes a convergent-divergent region, where the cross-section is taken along a longitudinal axis of the elongated body.

FIG. 4 is a cross-sectional view of a distal portion of another example of catheter 50 that includes elongated body 52 including a convergent-divergent region 60. As shown in FIG. 4, convergent-divergent region 60 may include one or more structural reinforcement elements 58 embedded within a wall of elongated body 52 (e.g., between layers of elongated body 52 or within one layer of material). In some examples, structural support element 58 may include a wire braid or a coil that surrounds the inner wall 64 of elongated body 52 that defines convergent-divergent region 60.

Structural support element 58 may help increase the structural rigidity of convergent-divergent region 60, which may help improve the navigability of catheter 50 through the vasculature of a patient and/or help increase the ability of wall 52 withstand the pressure differential of a fluid being passed through inner lumen 62. In some cases, structural support element 58 may also be configured to better distribute pressure throughout the elongated body of catheter 50, so as to minimize any adverse impacts on the structural integrity of catheter 50 during the cavitation process. Structural support element 58 may be formed from any suitable material. In some examples, structural support element 58 may include one or more metals, such as stainless steel or a nickel-titanium alloy (e.g., Nitinol), and may be in the form of one or more coils (e.g., a single coil wound in one direction, a single cross-wound coil, or multiple coils wound in the same or different directions), one or more braided members, or any combination thereof. In some examples, structural support element 58 may extend over convergent-divergent region 60 as well as other portions of the elongated body of catheter 50.

In some examples, convergent-divergent region 60 may include an outer casing 54 that forms the outer diameter (OD) of elongated body 52 of catheter 50 across convergent-divergent region 60. In some examples, outer casing 54 is a sheath that extends over the hour-glass shape 70 formed by the outer surface of inner wall 64 within convergent-divergent region 60, as well as any optional structural support elements 58. In some such examples, the outer diameter (OD) established by outer casing 54 may mimic the contour changes of convergent-divergent region 60, resulting in an hour-glass shaped outer diameter (OD) over convergent-divergent region 60. In other examples, outer casing 54 may provide a relatively smooth outer diameter (OD) over convergent-divergent region 60 such that the appearance of hour-glass shape 70 is reduced (e.g., smooth or nearly smooth transition in the outer diameter (OD) from the proximal to distal sides of convergent-divergent region 60).

In some examples, the area 78 between outer casing 58 and inner wall 64 within the region defined by hour-glass shape 70 may be filled with additional materials (e.g., additional casing, liner, or filler material, optional structural support elements 58, and the like) to form a substantially continuous outer diameter (OD) (e.g., an outer diameter that is either substantially constant or defines a smooth diameter gradient) as shown in FIG. 4. In some examples, the area 78 between outer casing 54 and inner wall 64 within the region defined by hour-glass shape 70 is filled with an inelastic or elastic material to provide further structural support to elongated body 52 within convergent-divergent region 60. In some examples, the outer diameter (OD) of elongated body 52 may be substantially constant (e.g., a constant or nearly constant outer diameter from the proximal to distal sides of convergent-divergent region 60). In other examples, the outer diameter (OD) of elongated body 52 may have a gradient 75 as depicted in FIG. 4, where the outer diameter (OD) continually increases or decreases from the proximal to distal sides of convergent-divergent region 60.

In some examples, the substantially continuous outer diameter created by outer casing 54 and, in some cases, fill material within area 78, may improve the deliverability of catheter 50 thorough the vasculature of a patient. Outer casing 54 may extend over the entire length of the elongated body of catheter 50 or may be localized to the distal portion or only convergent-divergent region 60. Suitable materials for outer casing 54 may include, for example, lubricious polymers such as PTFE, silicon doped polyether block amides (e.g., Pebax), or the like.

In some examples, a clinician may wish to occlude blood flow through vasculature 46 during a procedure, e.g., prior to and during treatment of lesion 44 (FIG. 3). In some examples, catheter 50 is sized (e.g., may have an outer dimension, such as an outer diameter) to provide some or complete occlusion of vasculature 46. In addition, or instead, catheter 50 may include one or more occlusion elements, such as balloon 66 shown in the example of FIG. 4. Balloon 66 may be positioned proximal to convergent-divergent region 60, such that balloon 66 may occlude blood flow past distal end 68 of catheter 50. Balloon 66 may be inflated to occlude flow within the vasculature of the patient during the cavitation procedure. In some examples, balloon 66 may be inflated by injecting a fluid through a second lumen (not shown) within the wall of elongated body 52. Additionally or alternatively, balloon 66 may be deployed to stabilize and/or restrain catheter 50 within the vasculature of a patient to help maintain the position of elongated body 52 relative to the lesion (e.g., lesion 44 of FIG. 3).

In some examples, the outer diameter of catheter 50 at the proximal side of convergent-divergent region 60 may be less than the outer diameter of catheter 50 at the distal side of convergent-divergent region 60 as shown in FIG. 4. Such examples may improve the trackability of catheter 50 through the vasculature of a patient. Additionally or alternatively, the smaller outer diameter of catheter 50 proximal to convergent-divergent region 60 may allow for the accommodation of additional features such as balloon 66. In some examples, a smaller outer diameter of catheter 50 proximal to convergent-divergent region 60 (e.g., outer diameter at convergent section 72) compared to the outer diameter of catheter 50 distal to convergent-divergent region 60 (e.g., outer diameter at divergent section 76) may correlate to first lumen diameter ($D_1$) being less than third lumen diameter ($D_3$).

In some examples, convergent-divergent region 60 may include one or more protuberances 65 within one or more of convergent section 72, neck section 74, or divergent section 76 of convergent-divergent region 60. Protuberances 65 are configured to agitate or otherwise delaminarize the flow of the fluid passing through convergent-divergent region 60 within lumen 62. In some examples, agitating the flow of the fluid passing through convergent-divergent region 60 effectively increases the Reynolds number of the fluid transitioning the fluid from a laminar to turbulent flow, which may affect the degree of cavitation of the fluid as it flows through convergent-divergent region 60. The more turbulent the flow, the greater the pressure drop will be as the fluid flows from convergent section 72 to neck section 74, resulting in a greater degree of cavitation for a given flow rate. In some examples, the inclusion of protuberances 65 can increase the degree of cavitation of the fluid without needing to increase the volumetric flow rate of the fluid through lumen 62.

Protuberances 65 are structures that extend into lumen 62, as shown in FIG. 4, and may have any suitable shape. Example protuberances 65 may include, for example, ridges, fins, divots, ripples, bumps, or the like to agitate the flow of the cavitating fluid. Protuberances 65 may be formed as part of elongated body 52 (e.g., may be integral with elongated body 52), such as during the process of making convergent-divergent region 60 (e.g., injection mold). In other examples, protuberances 65 may be formed separately from elongated body 52 and attached to an inner wall of elongated body 52.

As discussed above, catheters described herein may include one or more radiopaque markers, which may help a clinician determine the position of the respective catheter within vasculature of a patient. For example, a radiopaque marker may be positioned at neck section 74 of convergent-divergent region 60, or another position within convergent-divergent region 60. In addition, or instead, in some examples, catheter 50 may include a radiopaque marker 56 at the distal end 68 of elongated body 52. Radiopaque marker 56 may be on the outer surface, partially embedded within elongated body 52, or along the inner surface near the distal end 68 of elongated body 52. Radiopaque marker 56 may be formed from any suitable material, and may be in the form of a continuous ring, a discontinuous ring, or multiple segments that extend around, in, or within elongated body of catheter 50.

Catheters including convergent-divergent regions described herein are configured to be navigated through vasculature of a patient. In order to facilitate this, the distal end (e.g., distal end 68 of elongated body 52) of the catheter may be configured to have an atraumatic-tip composed of relatively soft materials (e.g., compared to the proximal portion of catheter 50), such as polyether block amides (e.g., Pebax®) or the like to help prevent minimize any adverse effects to the vasculature tissue as a clinician navigates the catheter through the vasculature towards a treatment site.

In some examples, a catheter including a convergent-divergent region described herein may be a guide catheter that acts as a conduit to help support a microcatheter or the delivery of one or more medical devices. In some such examples, the inner lumen (e.g., inner lumen 62 shown in FIG. 4) may be configured to receive one or more medical devices (e.g., stent, balloon, filter, or the like), deliver a therapeutic agent to a distal tissue site, remove thrombus (e.g., by aspiration) from the patient's vasculature, and the like or any combination thereof. Example therapeutic agents include, but are not limited to, an oxygenated medium or a pharmaceutical agent, which may be, for example, a vasodilator such as nifedipine or sodium nitroprusside, or a tissue plasminogen activator (t-PA), which can be used to assist with the breakdown lesions prior to or after the cavitation procedure.

In examples in which an inner lumen (e.g., inner lumen 62) defined by an elongated body of a catheter is used to remove portions of lesion 44 from vasculature, the catheter may be referred to as an aspiration catheter. During the aspiration process, a vacuum may be applied a proximal end of the elongated body of the catheter (e.g., at opening 15 of catheter 10) to draw portions of the dislodged lesion into the inner lumen of the catheter.

Figure 5:
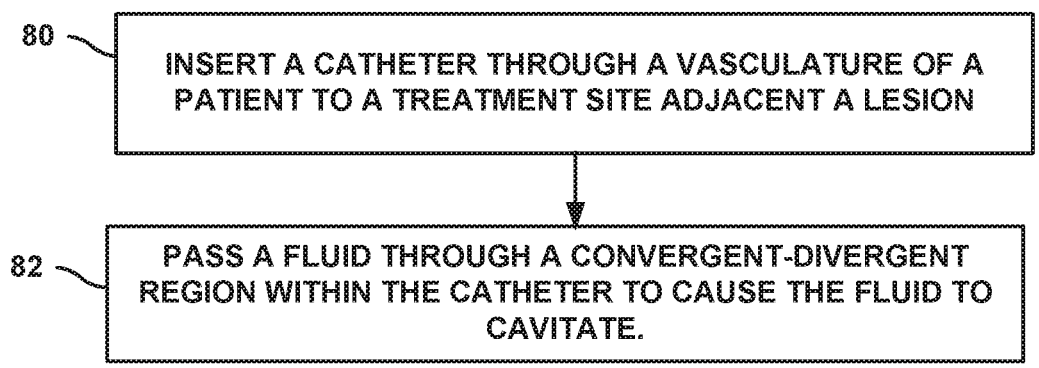
FIG. 5 is a flow diagram of an example technique of using the catheters described herein.

FIG. 5 is a flow diagram of an example technique of using catheter 10, 50. The technique of FIG. 5 is described with reference to FIGS. 1-4 for illustrative purposes, however, such descriptions are not intended to be limiting and the techniques of FIG. 5 may be used with other catheters or the catheter of FIGS. 1-4 may be used for other applications.

The technique of FIG. 5 includes introducing a catheter 10, 50 into a vasculature 46 of a patient to a treatment site adjacent to a lesion 44 (80). For example, a distal end 12B of the catheter 10, 50 may be positioned proximal to lesion 44. The distal end may, but need not to, touch lesion 44 in order for the cavitation of fluid 48 provided by catheter 10, 50 to break-up or otherwise disrupt lesion 44.

The technique further includes, after positioning the distal end of the catheter 10, 50 at the treatment site, passing a fluid 48 through an inner lumen 18, 62 and a convergent-divergent region 20, 60 of the catheter 10, 50 such that the convergent-divergent region 20, 60 causes fluid 48 flowing through lumen 18, 62 to cavitate as it flows through convergent-divergent region 20, 60 (82). As described above, the cavitation of fluid 48 causes the fluid to form cavitation gaseous bubbles 38 that subsequently implode 40 to form a pressure shockwave 42 that can be used to impact calcified lesion 44 causing the lesion to dislodge or break apart.

In some examples, introducing catheter 10, 50 into vasculature 46 of a patient to a treatment site adjacent to a lesion 44 (80) may include introducing a guide member (e.g., guidewire or guide catheter) into vasculature 46 (e.g., an intracranial blood vessel or a coronary artery) of a patient via an access point (e.g., a femoral artery) followed by introducing catheter 10, 50 over the guide member or within the guide member (e.g., in the case of an outer guide catheter). As described above, the neck section 34 of the convergent-divergent region 20, 60 defined by second lumen diameter ($D_2$) may be selectively sized to receive a guide member or guidewire to help advance catheter 10, 50 through the vasculature 46 of a patient towards the treatment site including lesion 44.

In some examples, passing fluid 48 through inner lumen 18, may include passing saline through convergent-divergent region 20, 60 at a flow rate of about 1 cc/s to about 20 cc/s.

Various examples have been described. These and other examples are within the scope of the following claims.

What is claimed is:

1. A catheter comprising:
an elongated body configured for navigation through vasculature of a patient, the elongated body comprising an inner wall that defines a lumen extending from a proximal portion to a distal portion, the elongated body configured to pass a fluid through the lumen and out an ejection port at a distalmost end of the catheter,
wherein at the distal portion of the elongated body, the inner wall defines a convergent-divergent region such that a diameter of the lumen while moving distally within the elongated body converges from a first lumen diameter to a second lumen diameter and then diverges from the second lumen diameter to a third lumen diameter, wherein the ejection port at the distalmost end of the catheter has a fourth lumen diameter that is greater than the second lumen diameter, wherein the convergent-divergent region is configured to cause the fluid flowing through the lumen at a target flow rate to cavitate and produce a pressure shockwave as the fluid flows through the convergent-divergent region, wherein the catheter is configured such that the fluid flowing out of the ejection port at the distalmost end of the catheter is unimpeded, and wherein the catheter is configured such that the pressure shockwave emerges from the ejection port at the distalmost end of the catheter.

2. The catheter of claim 1, wherein the convergent-divergent region comprises a cavitation region defined by the inner wall, the cavitation region having a length of about 0.5 millimeters (mm) to about 3 mm, wherein the length of cavitation region is an axial distance from a point where the second lumen diameter begins to diverge to the third lumen diameter to the distal end of the elongated body.

3. The catheter of claim 2, wherein the cavitation region comprises at least one radiopaque marker.

4. The catheter of claim 1, wherein a ratio of the third lumen diameter to the second lumen diameter is at least about 2.5:1.

5. The catheter of claim 1, wherein the elongated body defines a substantially continuous outer diameter along the convergent-divergent region.

6. The catheter of claim 1, wherein the elongated body defines an outer diameter along the convergent-divergent region having an hour-glass shape.

7. The catheter of claim 1, further comprising a balloon connected to the elongated body proximal to the convergent-divergent region.

8. The catheter of claim 1, wherein the elongated body further comprises a structural support element at the convergent-divergent region, the structural support element comprises at least one of a wire braid or a coil.

9. The catheter of claim 8, wherein the convergent-divergent region comprises a neck section defined by the second lumen diameter, wherein the structural support element surrounds the inner wall of the convergent-divergent region at the neck section.

10. The catheter of claim 1, further comprising an outer casing positioned over the inner wall, wherein the outer casing defines a substantially continuous outer diameter of the catheter along the convergent-divergent region.

11. The catheter of claim 10, wherein the convergent-divergent region comprises a neck section defined by the second lumen diameter, wherein a region between the inner wall at the neck section and the outer casing comprises an elastic or inelastic fill material.

12. The catheter of claim 1, wherein the elongated body comprises at least one protuberance extending into the lumen within the convergent-divergent region, wherein the at least one protuberance is configured to agitate the flow of the fluid that passes through the lumen.

13. The catheter of claim 12, wherein the at least one protuberance comprises a ridge, a fin, a divot, a bump, or a ripple in the inner wall.

14. The catheter of claim 1, wherein the fourth lumen diameter is approximately equal to the third lumen diameter.

15. The catheter of claim 14, wherein the diameter of the lumen between the third lumen diameter and the ejection port at the distalmost end of the catheter is substantially constant.

16. The catheter of claim 1, wherein the diameter of the lumen between the third lumen diameter and the ejection port at the distalmost end of the catheter does not converge.

17. The catheter of claim 1, wherein the convergent-divergent region is configured to cause a velocity of the fluid at a given flow rate to decrease and increase a hydrostatic pressure of the fluid as the fluid transitions within the lumen from a first portion of the lumen having the second lumen diameter to a second portion of the lumen having the third lumen diameter, and wherein the increase in the hydrostatic pressure of the fluid causes gaseous bubbles to implode within the lumen to release energy in the form of the pressure shockwave.

18. The catheter of claim 1, wherein, when the ejection port if positioned proximate to a calcified lesion, the pressure shockwave is configured to break up at least a part of the calcified lesion.

19. The catheter of claim 1, further comprising an outer casing positioned over the inner wall, wherein the outer casing does not extend distally beyond a distalmost end of the elongate body.

20. The catheter of claim 1, wherein the diameter of the lumen, while moving distally within the elongated body, converges from the first lumen diameter to the second lumen diameter non-linearly.

21. The catheter of claim 1, wherein the catheter is configured such that the pressure shockwave emerges from the ejection port at the distalmost end of the catheter to impact a lesion adjacent the ejection port.

22. An assembly comprising:
a catheter comprising an outer casing and an elongated body configured for navigation through vasculature of a patient, the elongated body comprising an inner wall that defines a lumen extending from a proximal portion to a distal portion, the elongated body configured to pass a fluid through the lumen and out an ejection port at a distalmost end of the catheter, wherein at the distal portion of the elongated body, the inner wall defines a convergent-divergent region such that a diameter of the lumen while moving distally within the elongated body converges from a first lumen diameter to a second lumen diameter and then diverges from the second lumen diameter to a third lumen diameter, wherein the ejection port at the distalmost end of the catheter has a fourth lumen diameter that is greater than the second lumen diameter, wherein outer casing positioned over the inner wall, and wherein the outer casing does not extend distally beyond a distalmost end of the elongate body; and a pump assembly connected to the proximal portion of the elongated body of the catheter and configured to pump a fluid at a target flow rate through the lumen of the elongated body and out the ejection port, wherein the convergent-divergent region of the elongated body is configured to cause the fluid flowing through the lumen at the target flow rate to cavitate and produce a pressure shockwave as the fluid flows through the convergent-divergent region, and wherein the catheter is configured such that the pressure shockwave emerges from the ejection port at the distalmost end of the catheter.

23. The assembly of claim 22, further comprising the fluid, wherein the fluid comprises saline.

24. The assembly of claim 22, the convergent-divergent region of the elongated body is configured to cause the fluid flowing at the target flow rate of about 1 cubic centimeters per second (cc/s) to about 20 cc/s to cavitate as the fluid flows through the convergent-divergent region.

25. The assembly of claim 22, wherein a ratio of the third lumen diameter to the second lumen diameter is at least about 2.5:1.

26. The assembly of claim 22, wherein the convergent-divergent region comprises a cavitation region defined by the inner wall having a length of about 0.5 mm to about 3 mm, wherein the length of cavitation region is an axial distance from a point where the second lumen diameter begins to diverge to the third lumen diameter to the distal end of the elongated body.

27. The assembly of claim 22, wherein the elongated body defines a substantially continuous outer diameter over the convergent-divergent region.

28. The assembly of claim 22, wherein the elongated body further comprises a structural support element at the convergent-divergent region, the structural support element comprising at least one of a wire braid or a coil.

29. The assembly of claim 28, wherein the elongated body further comprising an outer casing positioned over the inner wall and the structural support element, wherein the outer casing defines a substantially continuous outer diameter over the convergent-divergent region.

30. The assembly of claim 22, wherein the elongated body comprises at least one protuberance extending into the lumen within the convergent-divergent region, wherein the at least one protuberance is configured to agitate the flow of the fluid that passes through the lumen.

31. A method comprising:
positioning a distal end of a catheter adjacent to a lesion within a vasculature of a patient, wherein the catheter comprises an elongated body comprising an inner wall that defines a lumen extending from a proximal portion to a distal portion, the elongated body configured to pass a fluid through the lumen and out an ejection port at a distalmost end of the catheter, wherein at the distal portion of the elongated body, the inner wall defines a convergent-divergent region such that a diameter of the lumen while moving distally within the elongated body converges from a first lumen diameter to a second lumen diameter and then diverges from the second lumen diameter to a third lumen diameter, wherein the ejection port at the distalmost end of the catheter has a fourth lumen diameter that is greater than the second lumen diameter; and injecting a fluid into the lumen of the elongated body, wherein injecting the fluid into the lumen at a target flow rate causes the fluid to cavitate as the fluid flows through the convergent-divergent region of the elongated body to form bubbles, wherein the bubbles implode prior to the bubbles exiting out the ejection port and produce a pressure shockwave, wherein the catheter is configured such that the fluid exiting out of the ejection port at the distalmost end of the catheter is unimpeded, and wherein the catheter is configured such that the pressure shockwave emerges from the ejection port at the distalmost end of the catheter.

32. The method of claim 31, wherein injecting the fluid into the lumen of the elongated body comprises injecting the fluid at the target flow rate of about 1 cubic centimeters per second (cc/s) to about 20 cc/s.

33. The method of claim 31, wherein injecting the fluid into the lumen of the elongated body comprises injecting saline.

* * * * *